(12) United States Patent
Cho et al.

(10) Patent No.: US 7,822,459 B2
(45) Date of Patent: Oct. 26, 2010

(54) PET-MRI HYBRID SYSTEM

(75) Inventors: Zang Hee Cho, Incheon (KR); Cheol Ok Lee, Incheon (KR); Young Bo Kim, Seongnam-si (KR); Ja Weon Yun, Suwon-si (KR); Hyung Jin Ahn, Anyang-si (KR); Dong Sung Kim, Suwon-si (KR); Hong Shim, Suwon-si (KR)

(73) Assignee: Gachon University Of Medicine & Science Industry-Academic Cooperation Foundation, Incheon (KR)

( * ) Notice: Subject to any disclaimer, the term of this patent is extended or adjusted under 35 U.S.C. 154(b) by 366 days.

(21) Appl. No.: 11/840,347

(22) Filed: Aug. 17, 2007

(65) Prior Publication Data
US 2008/0045829 A1 Feb. 21, 2008

(30) Foreign Application Priority Data
Aug. 18, 2006 (KR) .................. 10-2006-0078062

(51) Int. Cl.
*A61B 5/05* (2006.01)
*A41B 13/00* (2006.01)

(52) U.S. Cl. .................. 600/407; 600/415; 600/411; 600/431; 5/601

(58) Field of Classification Search .......... 600/407, 600/415; 5/601, 613; 52/111, 79.7, 223.11
See application file for complete search history.

(56) References Cited

U.S. PATENT DOCUMENTS

| 7,167,739 B2* | 1/2007 | Van De Rijdt et al. ...... 600/415 |
| 2001/0003218 A1* | 6/2001 | Schaefer ...................... 5/601 |
| 2003/0078489 A1* | 4/2003 | DeSilets et al. ............. 600/407 |

\* cited by examiner

*Primary Examiner*—Eric F Winakur
*Assistant Examiner*—Helene Bor
(74) *Attorney, Agent, or Firm*—Patterson Thuente Christensen Pedersen, P.A.

(57) ABSTRACT

Embodiments of the present invention may provide a PET-MRI hybrid system capable of arranging a PET apparatus and an MRI apparatus in a line. An MRI room containing the MRI apparatus and a PET room containing the PET apparatus are provided at either side of a central waiting room as opposed to each other about the waiting room. A rail portion linearly extends from the PET room to the waiting room on their bottoms. Another rail portion linearly extends on the bottom of the MRI room. A transfer unit, which supports a subject lying thereon, travels along the rail portions of the waiting room, the MRI room and the PET room. A bridge unit is provided between the rail portion of the waiting room and the rail portion of the MRI room. The bridge unit provides a space for opening and closing a shield door of the MRI room and allows the transfer unit to be reciprocated between the waiting room and the MRI room by selectively connecting the rail portion of the waiting room and the rail portion of the MRI room.

15 Claims, 12 Drawing Sheets

PET-MRI HYBRID SYSTEM

The present application claims priority from Korean Patent Application No. 10-2006-0078062 filed on Aug. 18, 2006, the entire subject matter of which is incorporated herein by reference.

BACKGROUND

1. Field

The present invention generally relates to a PET-MRI hybrid system, and more particularly to a PET-MRI hybrid system that can arrange a PET apparatus and an MRI apparatus in a line.

2. Background

Recently, medical imaging technology has rapidly evolved in modern medical science due to developments in life science and molecular science. One of the most common imaging technologies is the Positron Emission Tomography (PET), wherein the metabolism of a human body is researched by using an isotope and nuclear medicine images are obtained. The other common imaging technology is the Magnetic Resonance Imaging (MRI), wherein anatomic variations of a human body are observed by utilizing the principle of Nuclear Magnetic Resonance (NMR).

PET allows the molecular variations in a specific region of a brain to be three-dimensionally observed by using a radioactive isotope bonded to a specific ligand, thereby allowing the action mechanism of a brain to be understood in terms of molecule and genetic engineering. MRI provides anatomical information with high resolution. Further, the functional MRI (FMRI) derived from MRI allows oxygen and an amount of bloodstream controlling it in the specific region according to nerve activation to be observed relatively easily compared to PET.

However, while PET allows the physiological and molecular variations of brain cells to be observed, it has a low resolution. MRI can provide the tomographic images of a brain with good resolution. However, it cannot provide any molecular and genetic variations. The fMRI also allows the variation of the bloodstream to be observed, although it cannot replace the functions of PET. Further, since PET and MRI use functionally and physically different principles, it is very difficult to integrate them. Moreover, since an ultra-high magnetic field is used for the ultra-high-resolution MRI (7.0 T), there can be a problem in that the normal operation of the PET system is disturbed by the magnetic field.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. Other embodiments of the present invention may readily suggest themselves to such skilled persons having the benefit of this disclosure.

Figure 1:
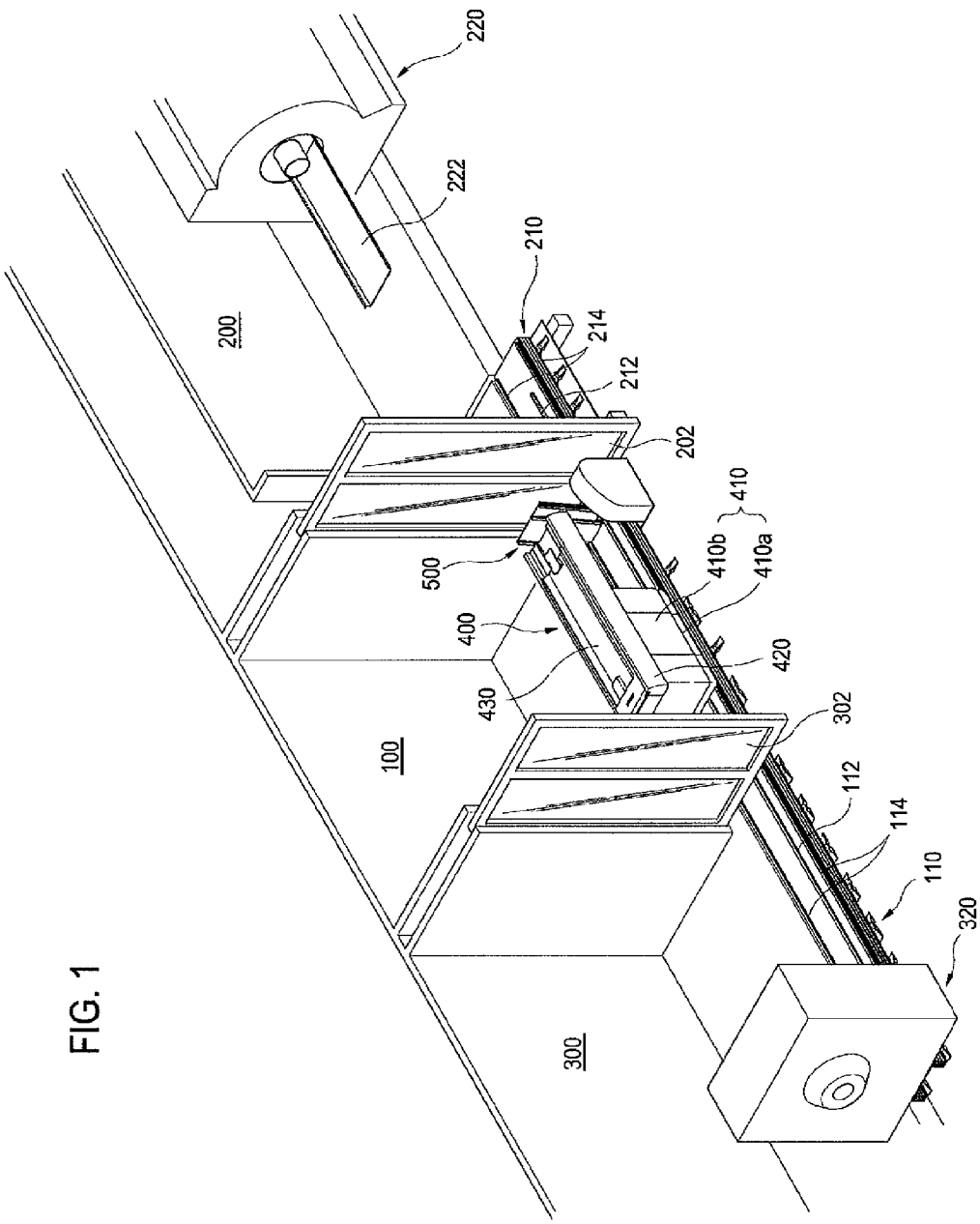
FIG. 1 schematically shows a PET-MRI hybrid system according to the present invention.

FIG. 1 schematically shows a PET-MRI hybrid system constructed in accordance with the present invention.

As shown in FIG. 1, the PET-MRI hybrid system of the present invention is configured such that a waiting room 100 is centrally located and a PET room 300, which contains a PET apparatus 320 therein, is located at the left side of the waiting room 100. Further, an MRI room 200, which contains an MRI apparatus 200 therein, is located at the right side of the waiting room 100. The MRI room 200, the waiting room 100 and the PET room 300 are arranged in a line.

A rail portion 110 extends from the PET room 300 to the waiting room 100 at their bottoms. Further, a rail portion 210, which is separated from the rail portion 110 of the waiting room 100, extends linearly at a bottom of the MRI room 200. The rail portion 110 of the waiting room 100 side and the rail portion 210 of the MRI room 200 side are arranged in a line. Each upper side of the rail portions 110 and 210 is provided in a lengthwise direction with at least one rack 112, 212 and a guide rail 114, 214.

On the upper sides of the rail portions 110, 210 are disposed a transfer unit 400 that linearly reciprocates along the rail portions 110, 210. The transfer unit 400 comprises a mover 410 and a shuttle table 420 provided on the mover 410. The mover 410 travels along the racks 112, 212 and the guide rails 114, 214. The shuttle table 420 generally has a hexahedral shape that is elongated in an extension direction of the rail portions 110, 210. An upper side of the shuttle table is opened. A cradle 430, on which a subject or a patient lies, is mounted to the upper side of the shuttle table 420.

A certain gap is formed between the rail portion 110 of the waiting room 100 side and the rail portion 210 of the MRI room 200 side. Said gap provides a space, through which a shield door 202 of the MRI room 200 slides. A bridge unit 500 is disposed in said gap. The bridge unit 500 selectively connects the rail portion 110 of the waiting room 100 side and the rail portion 210 of the MRI room 200 side.

Figure 2:
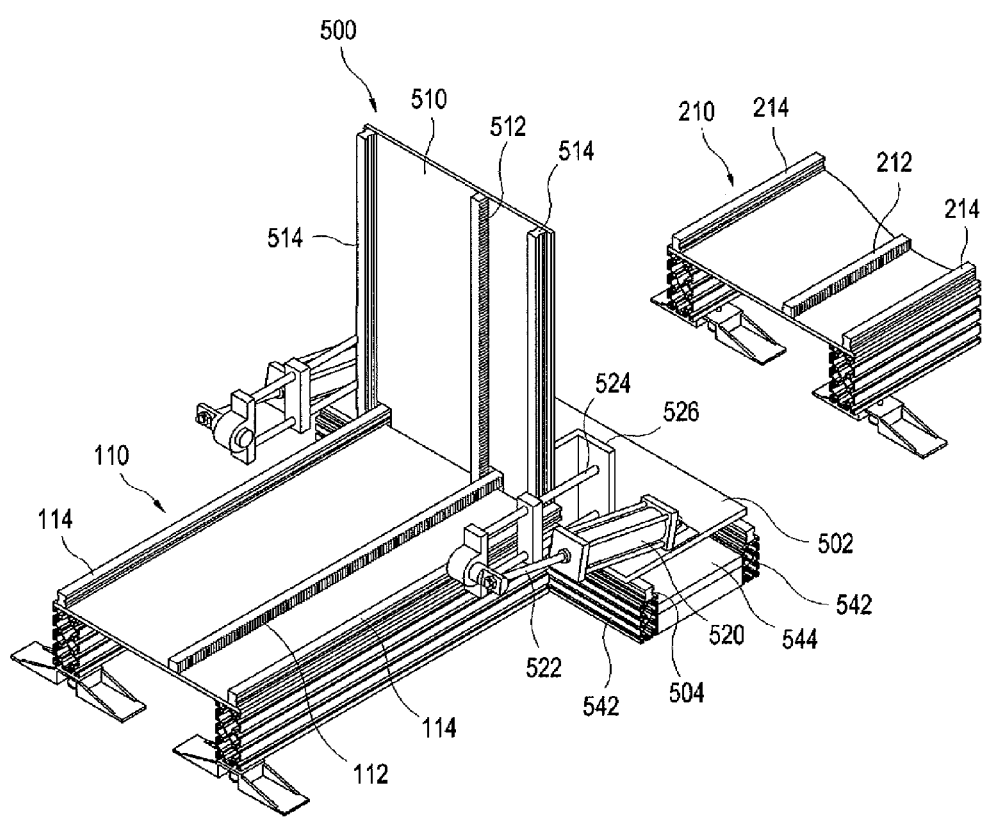
FIG. 2 is a perspective view of a bridge unit in the PET-MRI hybrid system according to the present invention.

As shown in FIG. 2, the bridge unit 500 comprises the following: a supporting plate 502 disposed adjacent to the rail portion 110 of the waiting room 100 side in the gap between the rail portion 110 of the waiting room 100 side and the rail portion 210 of the MRI room 200 side; a connecting plate 510 disposed on the supporting plate 502; a first pneumatic or hydraulic cylinder 520 pivotably coupled to one side of an upper side of the supporting plate 502 at one end thereof; a connecting rod 524 coupled to an end of a piston 522 at one end thereof and connected to the connecting plate 510 at the other end thereof; and a driving portion (not shown) for actuating the piston 522 of the first cylinder 520. The connecting rod 524 and the connecting plate 510 are connected by a plate-like bracket 526. Preferably, a couple of the cylinder 520 and the connecting rod 524 are disposed at left and right lateral sides of the connecting plate 510, respectively. The upper surface of the connecting plate 510 is provided with a rack 512 and a guide rail 514, which correspond to the rack 112, 212 and the guide rail 114, 214 of the rail portion 110, 210 respectively.

Figure 3:
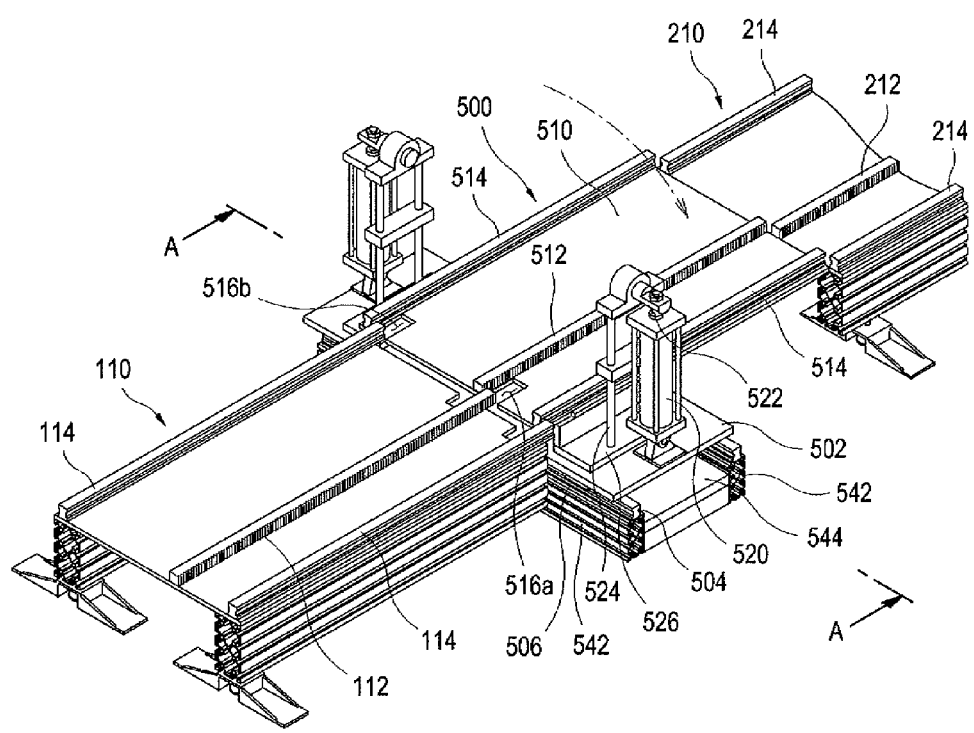
FIG. 3 is a perspective view showing one operation of the bridge unit.

When the connecting plate 510 is upright as shown in FIG. 2, if the piston 522 of the first cylinder 520 is pulled into the cylinder 520 by an operation of the driving portion, then the first cylinder 520 and the connecting rod 524 linked to the leading end of the piston 522 are vertically situated, while the connecting plate 510 connected to the connecting rod 524 is horizontally situated (shown in FIG. 3). This is possible because the piston 522 of the first cylinder 520 and the connecting rod 524 are positioned so as to be apart from each other at their central axes.

As shown in FIG. 3, although the connecting plate 510 is horizontally situated by the actuation of the first cylinder 520, the rack 512 and the guide rail 514 provided on the connecting plate 510 and the rack 112, 212 and the guide rail 114, 214 on the rail portion 110, 210 are situated so as not to coincide with each other. This is so that the rack 512 and the guide rail 514 provided on the connecting plate 510 and the rack 112, 212 and the guide rail 114, 214 on the rail portion 110, 210 are not separated and can be successively connected when the connecting plate 510 is horizontally situated. The connecting plate 510 is formed with notches 516a and 516b. When the connecting plate 510 is vertically situated, the rack 112 and the guide rail 114 of the waiting room 100 side do not contact the connecting plate 510 due to the notches 516a and 516b.

In order to align the rack 512 and the guide rail 514 provided on the connecting plate 510 and the rack 112, 212 and the guide rail 114, 214 on the rail portion 110, 210 in a line, the connecting plate 510 and the supporting plate 502 are shifted in a widthwise direction of the rail portion 110, 210. To facilitate the horizontal shift of the supporting plate 502, a plurality of guide rails 504 are provided under a lower side of the supporting plate 502 in a widthwise direction. Further, a plurality of moving blocks 506, which have a configuration mating to the guide rail 504, are mounted to the lower side of the supporting plate 502. The guide rails 504 are mounted on supporting frames 542 lying transverse to the guide rail 114, 214. The supporting frames 542 are joined to each other by a fixing plate 544.

Figure 5:
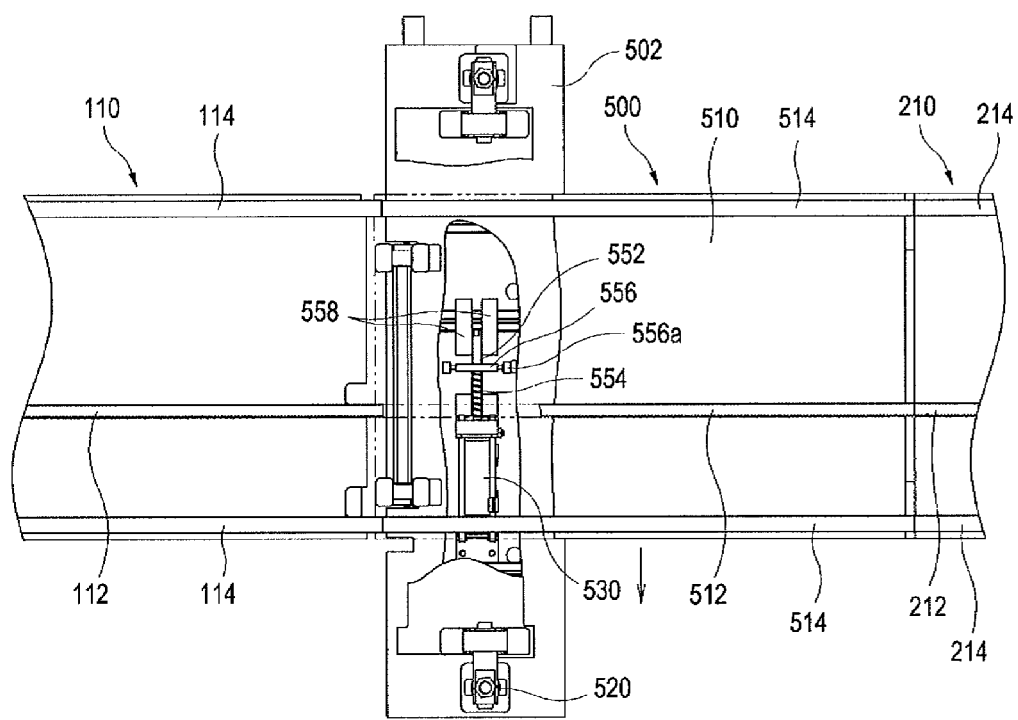
FIG. 5 is a partially cutaway plan view showing the aligned bridge unit.
Figure 6:
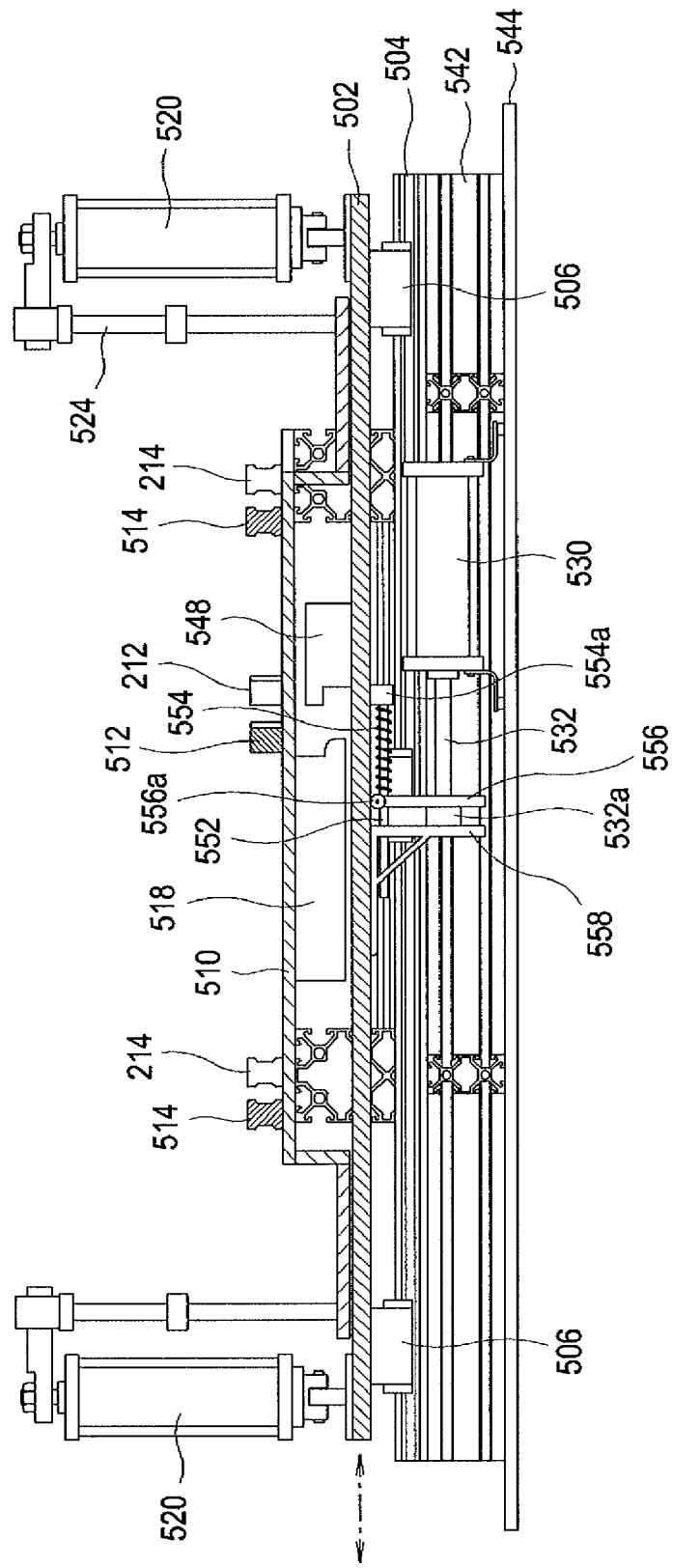
FIG. 6 is a sectional view taken along the line A-A of FIG. 3.

FIG. 5 is a partially cutaway plan view of the bridge unit, which shows a constitution for transversely shifting the connecting plate 510 and the supporting plate 502. FIG. 6 is a sectional view taken along the line A-A of FIG. 3.

As shown in FIGS. 5 and 6, a second pneumatic or hydraulic cylinder 530, which has a piston 532 movable by the driving portion (not shown), is mounted on the fixing plate 544 in a widthwise direction. The connecting plate 510 and the supporting plate 502 are horizontally shifted by the actuation of the second cylinder 530.

A leading end 532a of the piston 532 and the supporting plate 502 are connected to each other by a movable plate 556 and an angle member 558. The angle member 558 has an L-shaped cross section and is fixed to the lower side of the supporting plate 502. The movable plate 556 has a roller 556a at a top thereof and is fixed to the leading end 532a of the piston 532 at a bottom thereof. The roller 556a is in rolling contact with the lower side of the supporting plate 502.

The movable plate 556 is moved along a guide rod 552. The guide rod 552 is fixed to a spring holder 554a fixed to the lower side of the supporting plate 502 at one end thereof and is joined to the angle member 558 at the other end thereof. The guide rod 552 passes through an upper side of the movable plate 556. A spring 554 is disposed between the movable plate 556 and the spring holder 554a as winding around the guide rod 552. The spring 554 is disposed as slightly compressed.

The lower side of the connecting plate 510 is provided with a first stopper 518. A portion of the supporting frame 542 is provided with a second stopper 548, which restricts the movements of the supporting plate 502 and the connecting plate 510 by contacting the first stopper 518. The first stopper 518 and the second stopper 548 are positioned such that they contact each other when the rack 512 and the guide rail 514 of the connecting plate 510 and the rack 112, 212 and the guide rail 114, 214 on the rail portion 110, 210 are aligned in a line by shifting the supporting plate 502.

If the piston 532 of the second cylinder 530 is pulled into the second cylinder 530, then the leading end 532a of the piston 532 is moved to the right as shown in FIG. 6. At the same time, the movable plate 556 is also moved to the right. Then, the supporting plate 502 is moved to the right as the spring 554 is slightly compressed. Thus, the connecting plate 510 is shifted from a non-aligned state (see FIG. 3) to an aligned state (see FIG. 4), as shown by the arrow in FIG. 5. If the first stopper 518 contacts the second stopper 548, then the supporting plate 502 is stopped. The second cylinder 530 is further actuated so as to pull the piston therein after the first stopper 518 contacts the second stopper 548. Since the spring 554 serves to press the spring holder 554a from the movable plate 556 to the right in FIG. 6, the supporting plate 502 is maintained at the alignment state after a pull stroke of the cylinder 530 for pulling the piston is completed. When the pull stroke of the cylinder 530 is completed, the leading end 532a of the piston 532 can be located farther than a contact point of the first stopper 518 and the second stopper 548 due to the spring 554.

Figure 4:
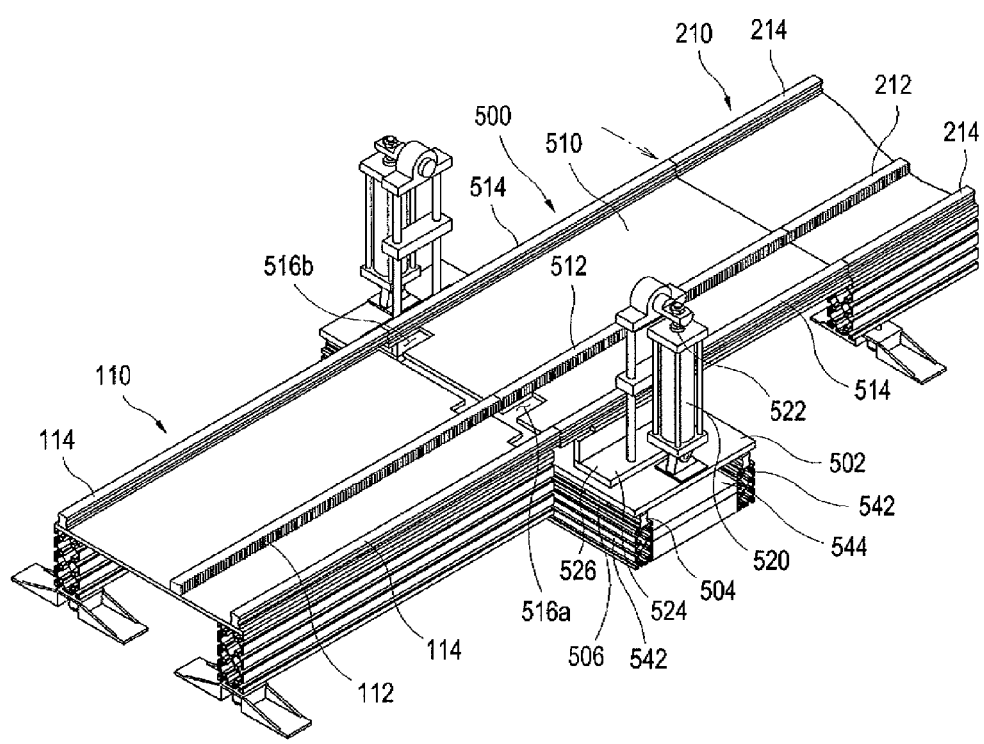
FIG. 4 is a perspective view showing another operation of the bridge unit.

In case of shifting the supporting plate 502 from the aligned state of FIG. 4 to the non-aligned state, the second cylinder 530 starts a push stroke. Then, the leading end 532a of the piston 532 contacts the angle member 558 and the supporting plate 502 is shifted from the aligned state to the non-aligned state (see FIG. 3) by the push stroke of the second cylinder 530. When the push stroke of the cylinder 530 is completed, the supporting plate 502 is maintained at that position. Since the expansion force of the spring 554 acts between the movable plate 556 and the spring holder 554a, the supporting plate 502 is restricted from being away from the position of the leading end 532a of the piston 532 after the push stroke of the cylinder 530 is ended. Thereafter, the connecting plate 510 is moved to the vertical state of FIG. 2 by the cooperation of the first cylinder 520 and the connecting rod 524, as described above.

Figure 7:
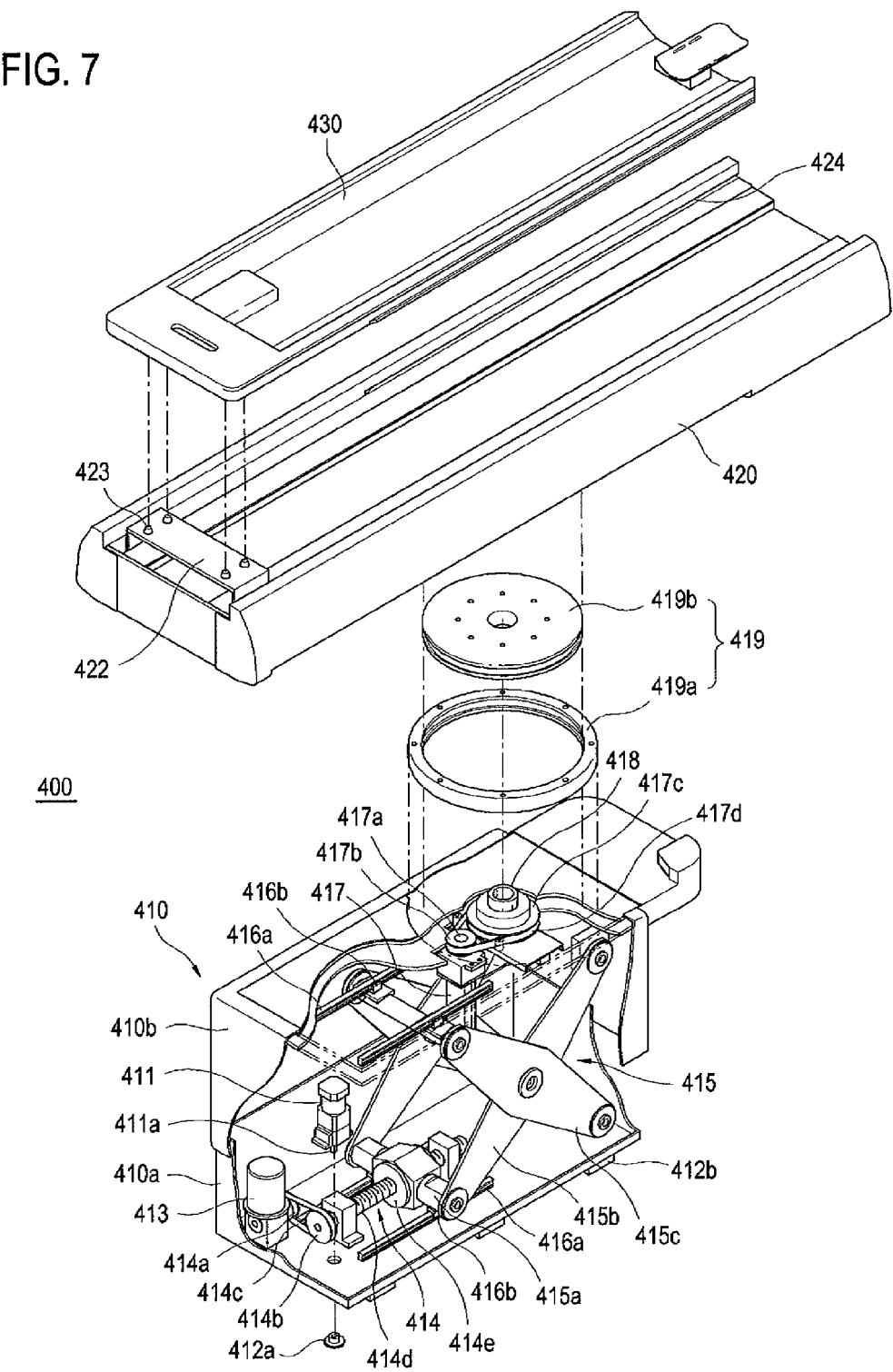
FIG. 7 is an exploded perspective view of a transfer unit in the PET-MRI hybrid system according to the present invention.

As shown in FIG. 7, the mover 410 of the transfer unit 40 comprises a lower section 410a and an upper section 410b. The lower section 410a is located on the rail portion 110, 210. The upper section 410b covers an upper side of the lower section 410a and is coupled thereto to be upwardly and downwardly movable. A back side of a bottom plate of the lower section 410a is provided with a spur gear 412a and a plurality of moving blocks 412b. The spur gear 412a is engaged to the racks 112, 212 of the rail portions 110, 210 and the rack 512 of the bridge unit 500. The moving block 412b is formed so as to correspond to the guide rails 114, 214, 514. An inside of the mover 410 is provided with a first driving means 411 for rotating the spur gear 412a. The spur gear 412a is joined to an end of a driving shaft 411a.

Further, the inside of the mover 410 is provided with a second driving means 413, a first converting means 414 and a second converting means 415. The second driving means 413 generates a driving force for lifting and lowering the upper section 410b relative to the lower section 410a. The first converting means 414 converts the rotation force caused by the second driving means 413 into linear motion. The second converting means 415 links the first converting means 414 to the upper section 410b and converts the linear motion of the first converting means 414 into lifting and lowering motion of the upper section 410b.

More specifically, the first converting means 414 comprises: a driving pulley 414a coupled to a leading end of the driving shaft (not shown) of the second driving means 413; a driven pulley 414b rotatably disposed on the bottom of the lower section 410a; a belt 414c winding between the driving pulley 414a and the driven pulley 414b to rotate them together; a lead screw 414d coupled to a center of the driven pulley 414b at one end thereof to be rotated together with the driven pulley 414b and being elongated in an extension direction of the rail portion 110, 210; and a nut 414e screw-engaged to the lead screw 414d to be linearly moved by the rotation of the lead screw 414d.

The second converting means 415 comprises: a connecting shaft 415a coupled to at least one side of the nut 414e and extending at a right angle with the lead screw 414d; a first link 415b pivotably coupled to the connecting shaft 415a at a lower end thereof and pivotably coupled to one side of the upper section 410b at an upper end thereof, and a second link 415c cross-linked to a central portion of the first link 415b in an X-shape and pivotably coupled to the bottom of the lower section 410a at a lower end thereof and pivotably coupled to the other side of the upper section 410b at an upper end thereof.

According to the above-described conversion mechanism, if the second driving means 413 is operated, then the nut 414e is linearly moved along the lead screw 414d as the lead screw 414d is rotated. Further, the lower end of the first link 415b, which is connected to the nut 414e by the connecting shaft 415a, is caused to be linearly moved together with the nut 414d. For example, when the lower end of the first link 415b is linearly moved away from the lower end of the second link 415c, both the upper ends of the first link 415b and the second link 415c are lowered by the X-shaped cross linkage of the first link 415b and the second link 415c. On the contrary, when the lower end of the first link 415b is linearly moved so as to approach the lower end of the second link 415c, all of the upper ends of the first link 415b and the second link 415c and the upper section 410b coupled thereto are lifted by the X-shaped cross linkage of the first link 415b and the second link 415c.

To ensure the stable lift and lowering of the upper section 410b, it is preferable that two combinations of the first and second links 415b and 415c, which are crosslinked to each other in an X-shape, are symmetrically disposed at both lateral sides of the nut 414e. Further, it is preferable that straight guide rails 416a parallel to the lead screw 414d are provided on the bottom plate of the lower section 410a and under the top plate of the upper section 410b. Also, it is preferable that moving blocks 416b, which are engaged to the guide rails 416a and linearly slide therealong, are coupled to the lower end of the first link 415b and the upper end of the second link 415c.

The shuttle table 420 is mounted on the mover 410 so as to be horizontally slued at an angle of at least 180°. In order to slue the shuttle table 420, a third driving means 417 is provided in close proximity of the top plate of the upper section 410b and a driving pulley 417b is coupled to a driving shaft 417a of the third driving means 417. A wire race bearing 419 is mounted on the top plate of the upper section 410b. The wire race bearing 419 includes: an outer ring 419a fixed to the top plate of the upper section 410b; and an inner wheel 419b rotatably coupled to the outer ring 419a with balls disposed between its outer periphery and an inner periphery of the outer ring 419a. A cylinder-shaped rotating shaft 418 is coupled to a center of the inner wheel 419b as passing through it. A driven pulley 417c is coupled to a lower end of the rotating shaft 418. A belt 417d winds around the driving pulley 417b and the driven pulley 417c in order to rotate them together. The inner wheel 419b of the wire race bearing 419 has a height higher than that of the outer ring 419a to thereby protrude slightly over the outer ring 419a. The shuttle table 420 is joined to an upper surface of the inner wheel 419b to be slued together with the inner wheel 419b.

According to above-described constitution, if the third driving means 417 is operated, then a driving force of the third driving means 417 is transmitted through the driving pulley 417b, the belt 417d and the driven pulley 417c to the rotating shaft 418. Then, the shuttle table 420 is slued together with the inner wheel 419b when the inner wheel 419b coupled to the rotating shaft 418 is stably supported by the outer ring 419a.

An inside of a side wall of the shuttle table 420 is provided in a lengthwise direction with guide grooves 424 for guiding the movements of the cradle 430. A transfer plate 422 for transferring the cradle 430 is provided to be reciprocated along the guide grooves 424. A plurality of protrusions 423 are provided on an upper surface of the transfer plate 422. A plurality of insertion holes (not shown) are provided on a lower side of the cradle 430 at a location corresponding to the protrusions 423. The inside of the shuttle table 420 may be provided with a driving means (not shown) for linearly moving the transfer plate 422 and a transmission means (not shown) for transmitting a driving force of said driving means to thereby reciprocate the transfer plate 422. Since such a mechanism for transferring the cradle may be variously embodied, a detailed description regarding the structure of such a mechanism is omitted herein.

The operation process of the PET-MRI hybrid system, which is constructed in accordance with the above, will now be described.

As shown in FIG. 1, a waiting mode of the PET-MRI hybrid system of the present invention is a state where the upper section 410b and the shuttle table 420 of the transfer unit 400 are positioned to be lowered so that a subject can easily lie on the cradle 430. Further, it is a state where all of the shield doors 202 and 302 of the MRI room 200 and the PET room 300 are closed. In the waiting mode, the subject lies on the cradle 430 of the transfer unit 400 in an orientation wherein its head is directed to the MRI room 200.

Figure 8:
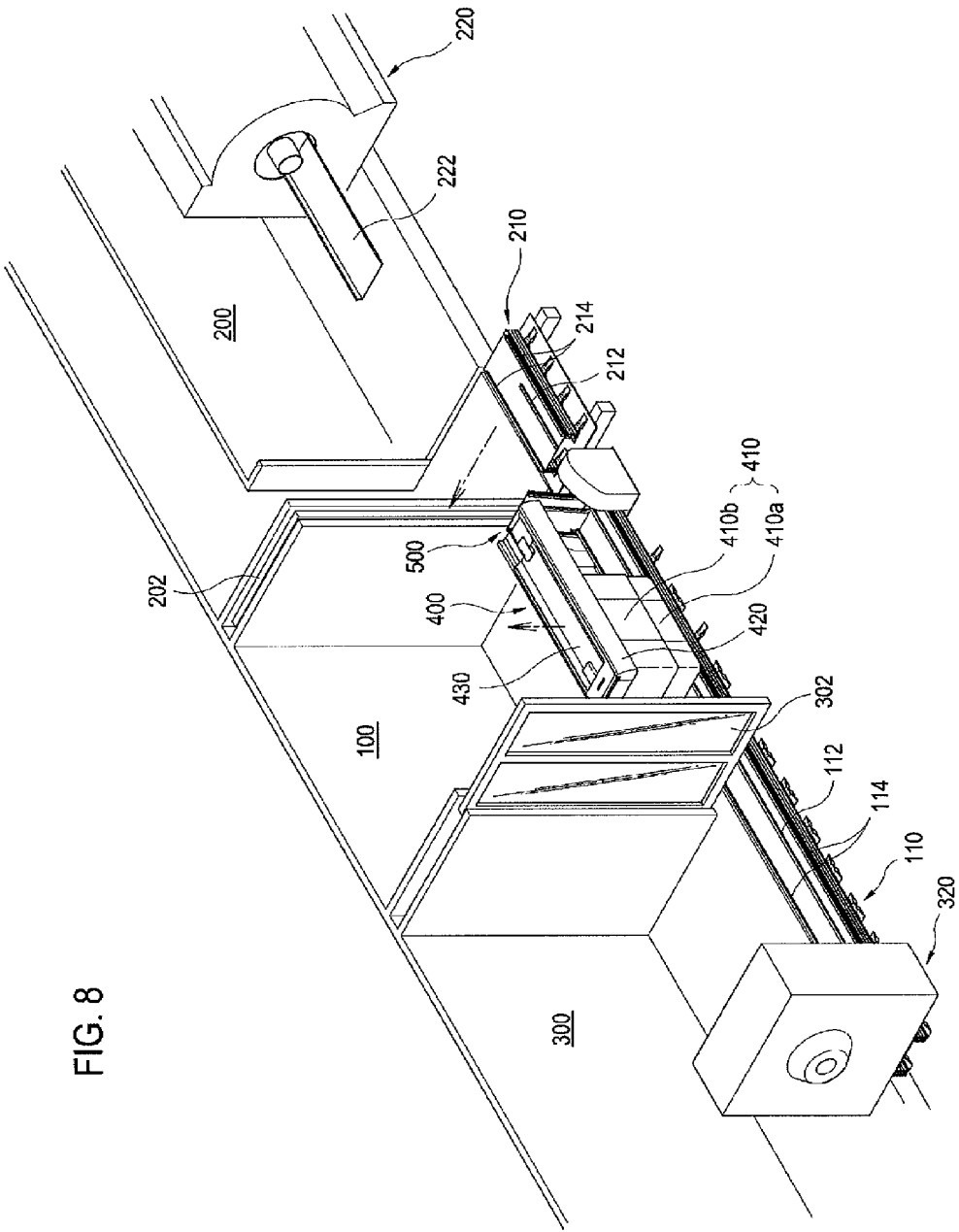
FIGS. 8 and 12 are perspective views showing the operation processes of the PET-MRI hybrid system.

As shown in FIG. 8, the closed shield door 202 of the MRI room 200 is opened and the second driving means 413 (see FIG. 7) is operated. The driving force of the second driving means is converted into the linear motion of the nut 414e relative to the lead screw 414d. Therefore, the upper section 410b is lifted from the lower section 410a by the action of the X-shaped crosslinked the first and second links 415b and 415c. In such a case, the lift height of the upper section 410b is determined such that the cradle 430 can be seated on an examination table 222 of the MRI apparatus 220.

Figure 9:
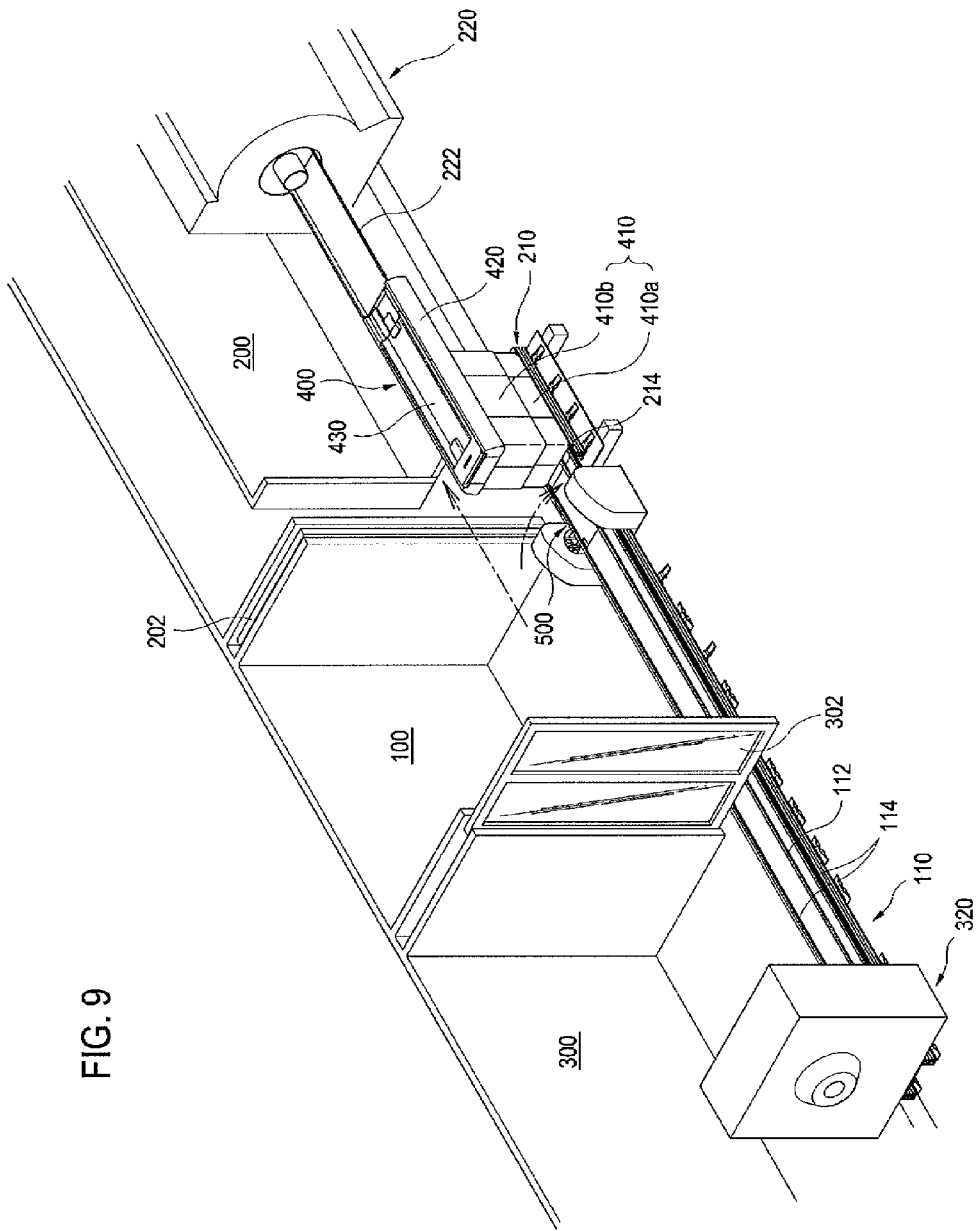

As shown in FIG. 9, the connecting plate 510 of the bridge unit 500, which is vertically situated when the shield door 202 of the MRI room 200 is closed, is pivoted by the action of the first cylinder 520 (see FIG. 3) and the connecting rod 524 to thereby be horizontally situated. Also, it is aligned with the rail portions 110 and 210 by the action of the second cylinder 530 (see FIG. 5). Next, the first driving means 411 (see FIG. 7) is operated for transferring the transfer unit 400. The driving force of the first driving means 411 causes the spur gear 412a, which is provided on the back side of the bottom plate of the lower section 410a, to rotate. Then, the mover 410 is moved from the rail portion 110 of the waiting room 100 through the connecting plate 510 of the bridge unit 500 to the rail portion 210 of the MRI room 200 by the action of the rotating spur gear 412a and the rack 112 engaged thereto, which is provided on the upper side of the rail portion 110 of the waiting room 100. In such a case, the mover 410 can be moved more stably due to the guide rails 114, 215 and 514 and the moving blocks 412b mounted to the lower section 410a of the mover 410.

Figure 10:
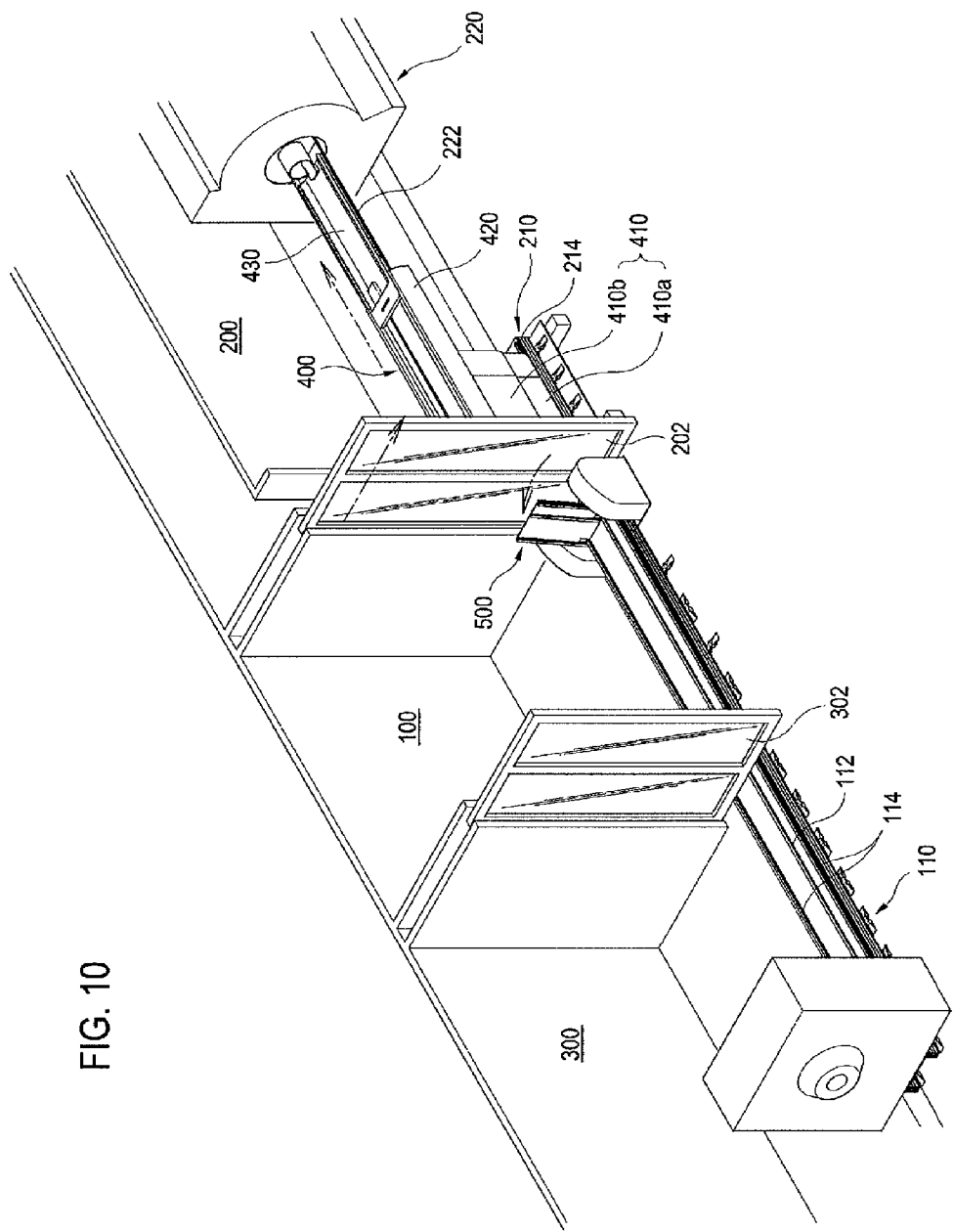

As shown in FIG. 10, if the mover 410 is completely moved inside the MRI room 200, then the horizontally situated connecting plate 510 of the bridge unit 500 is caused to be misaligned with the rail portions 110 and 210 by the action of the second cylinder 530. Then, it is vertically situated by the action of the first cylinder 520 and the connecting rod 524. Also, the opened shield door 202 of the MRI room 200 is closed. Thus, the MRI room 200 is isolated from the outside. This is so that an ultra-high magnetic field to be generated by the MRI apparatus 220 can be prevented from having any bad influence upon a normal operation of the PET apparatus 320.

After the shield door 202 of the MRI room 200 is completely closed, the transfer plate 422 mounted to the shuttle table 420 is moved toward the MRI apparatus 220. Further, the cradle 430 mounted on the shuttle table 420 is transferred by the moving transfer plate 422 to be seated on the examination table 222 of the MRI apparatus 220. Thereafter, the upper section 410b of the transfer unit 410 is slightly lowered so that the protrusions 423 of the transfer plate 422 are completely separated from the insertion holes of the cradle 430.

The examination table 222 with the cradle 430 seated thereon is pulled into the inside of the MRI apparatus 220 and the examination of a subject is then performed. After the examination, the cradle 430 and the examination table 222 is pulled out of the MRI apparatus 220. The upper section 410b of the mover 410 is then lifted up to the initial position and the protrusions 423 of the transfer plate 422 are fitted into the insertion holes provided on the lower side of the cradle 430. As the transfer plate 422 is moved away from the MRI apparatus 220, the cradle 430 is transferred from the upper side of the examination table 222 to the upper side of the shuttle table 420.

Figure 11:
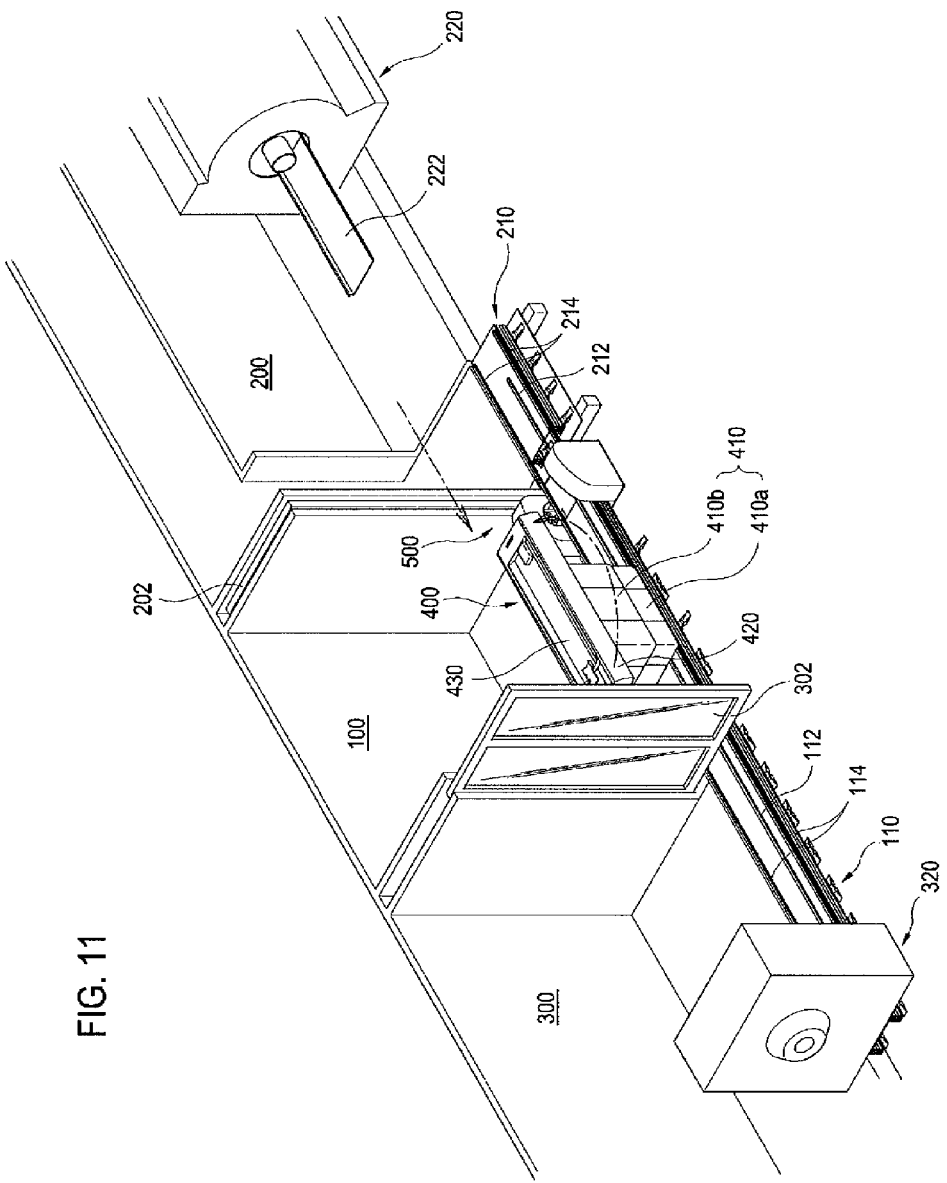

Thereafter, as shown in FIG. 11, the closed shield door 202 of the MRI room 200 is opened. Further, the vertically situated connecting plate 510 of the bridge unit 500 is pivoted to be horizontally situated, thereby connecting the rail portion 210 of the MRI room 200 and the rail portion 110 of the waiting room 100.

The first driving means 411 for transferring the transfer unit 400 is operated. The driving force of the first driving means 411 causes the spur gear 412a to rotate. Then, the mover 410 is moved from the rail portion 210 of the MRI room 200 through the connecting plate 510 of the bridge unit 500 to the rail portion 110 of the waiting room 100 by the action of the rotating spur gear 412a and the rack 212 engaged thereto, which is provided on the upper side of the rail portion 210 of the MRI room 200.

After the transfer unit 400 is located in the waiting room 100, the first driving means 411 is stopped and the transfer unit 400 thus stays in the waiting room 100. Further, the connecting plate 510 of the bridge unit 500 is pivoted so as to be vertically situated. Thereafter, the third driving means 417 is operated for slueing the shuttle table 420. The driving force of the third driving means 417 causes the shuttle table 420 to be horizontally slued at 180° through the wire race bearing 419. This is so that the head of a subject turns from the MRI room 200 toward the PET room 300. The shield door 202 of the MRI room 200 is closed and the shield door 302 of the PET room 300 is then opened.

Figure 12:
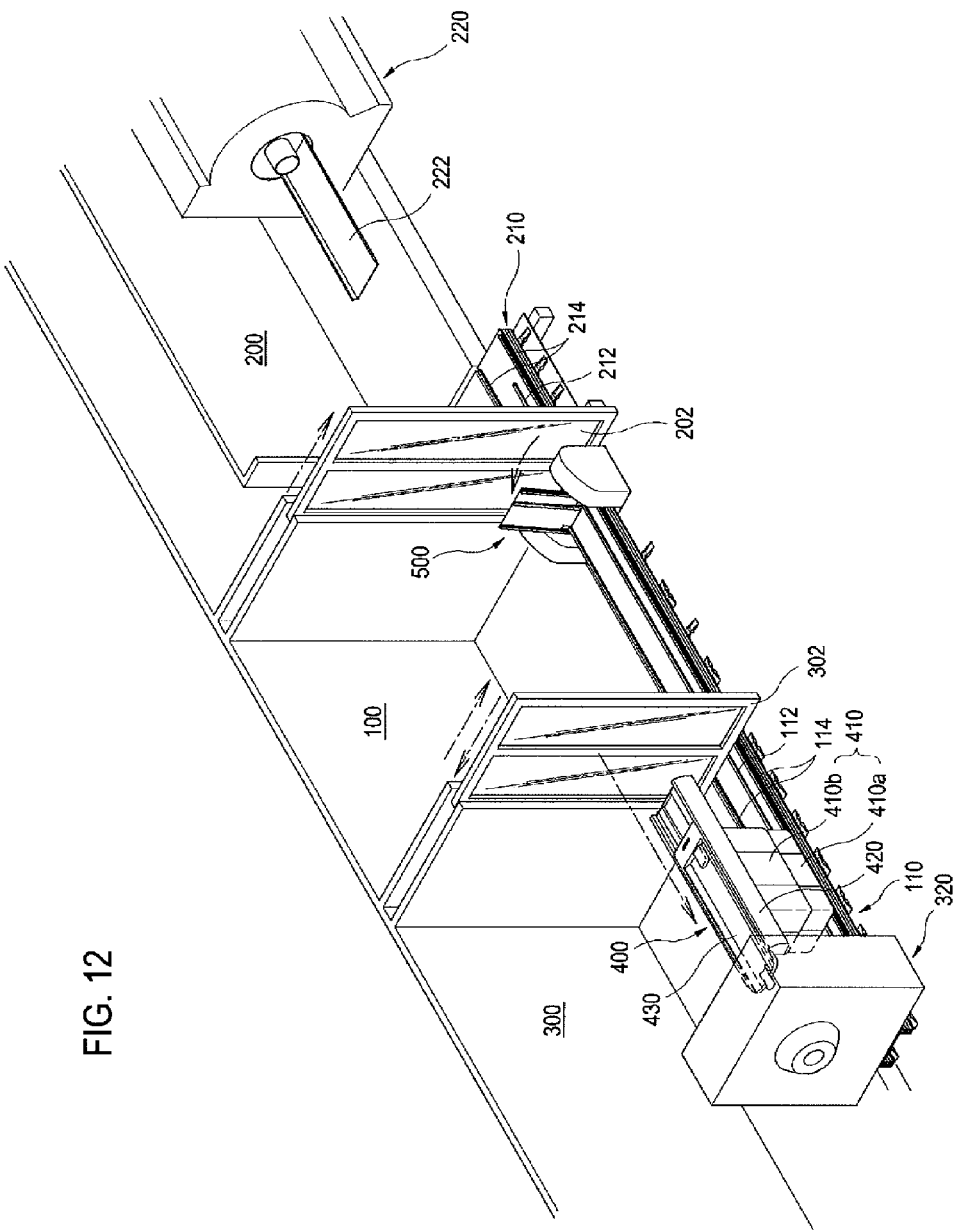

As shown in FIG. 12, the transfer unit 400 is moved into the PET room 300 and is stopped by the operation of the first driving means 411. The shield door 302 of the PET room 300 is then closed again. The transfer plate 422 mounted on the shuttle table 420 is driven such that a portion of the cradle 430 is located to an examination part of the PET apparatus 320. After an examination in the PET apparatus 320 ends, the transfer plate 422 is caused to return to its initial position. This is so that the cradle, a portion of which is pulled into the PET apparatus 320, can return to the shuttle table 420.

The shield door 302 of the PET room 300 is opened and the transfer unit 400 returns to the waiting room 100 by the operation of the first driving means 411. The shield door 302 of the PET room 300 is closed and the upper section 410b of the mover 410 is lowered to its lowermost position by the operation of the second driving means 413. Accordingly, the PET-MRI hybrid system returns to the waiting mode shown in FIG. 1.

Embodiments of the present invention may provide a PET-MRI hybrid system. The PET-MRI hybrid system arranges a PET apparatus and an MRI apparatus in a line and prevents an ultra-high magnetic field generated by the MRI apparatus from having any undesired influences on the PET apparatus and allows a subject to be minimally transferred to thereby accomplish a rapid examination. Since the genetic and molecular variations of brain cells can be shown as ultra-high resolution MRI 3D images based on the combined advantages of an MRI and a PET, the development of a brain disease, such as a brain tumor, Alzheimer's, cerebral hemorrhage, etc., as well as a melancholia, schizophrenia, autism, etc., can be prevented by detecting the molecular variations in advance. Further, the abnormalities in the genetic stage can be found earlier by visually observing the function of the gene.

A PET-MRI hybrid system may be provided. The PET-MRI hybrid system may comprise: a waiting room having a rail portion at a bottom thereof; an MRI room containing an MRI apparatus and having a rail portion aligned with the rail portion of the waiting room at a bottom thereof, the MRI room being divided from the waiting room by a shield door; a PET room containing a PET apparatus, the PET room being positioned to be opposed to the MRI room about the waiting room, wherein the rail portion of the waiting room is extended on a bottom of the PET room; a transfer unit for supporting a subject lying on an upper side thereof and traveling along the rail portions of the waiting room, the MRI room and the PET room; and a bridge unit for providing a space for movement of the shield door between the rail portion of the waiting room and the rail portion of the MRI room and allowing the transfer unit to be reciprocated between the waiting room and the MRI room by selectively connecting the rail portion of the waiting room and the rail portion of the MRI room.

Each upper side of the rail portions of the waiting room and the MRI room may be provided with at least one rack extending in a lengthwise direction of the rail portions. The transfer unit may comprise a gear engaged to the rack and a first driving means for generating a driving force for rotating the gear.

Each upper side of the rail portions of the waiting room and the MRI room may be provided with at least one guide rail extending in a lengthwise direction of the rail portions. The transfer unit may further comprise a plurality of moving blocks movable along the guide rail as contacted to the guide rail.

The transfer unit may comprise: a mover movable along the rail portions; a shuttle table horizontally sluably mounted to an upper side of the mover; and a cradle slidably mounted on an upper side of the shuttle table.

The mover may be composed of a lower section movable as contacted to the rail portions and an upper section covering an upper side of the lower section and being upward and downward movably mounted to the lower section.

The mover may be provided with the following: a second driving means for generating a driving force for lifting and lowering the upper section from and to the lower section; a first converting means for converting the driving force of the second driving means into linear motions; and a second converting means for linking the first converting means to the upper section and converting the linear motions of the first converting means into upward and downward motions.

The first converting means may comprise: a driving pulley rotatable by the second driving means; a driven pulley rotatably disposed on a bottom plate of the lower section; a belt winding around the driving pulley and the driven pulley; a lead screw coupled to a center of the driven pulley at one end thereof to be rotated together therewith and being elongated in an extension direction of the rail portions; and a nut screwed to the lead screw and being linearly moved by a rotation of the lead screw.

The second converting means may comprise: a connecting shaft coupled to at least one side of the nut and being horizontally extended perpendicular to the lead screw; a first link rotatably coupled to the connecting shaft at a lower end thereof and being rotatably coupled to one side of the upper section at an upper end thereof; and a second link cross-linked to a central portion of the first link and being rotatably coupled to the bottom of the lower section at a lower end thereof and being rotatably coupled to other side of the upper section at an upper end thereof.

A bottom plate of the lower section and a top plate of the upper section may be provided with guide rails extending in a lengthwise direction of the lead screw. The lower end of the first link and the upper end of the second link may be provided with moving blocks movable along the guide rails as contacted to the guide rail.

The mover may be provided with the following: a third driving means for generating a driving force for horizontally slueing the shuttle table; a driving pulley rotatable by the third driving means; a driven pulley connected to the drive pulley by a belt to be rotated together with the driving pulley; a rotating shaft coupled to a center of the driven pulley at one end thereof to be rotated together with the driven pulley; and a wire race bearing including an outer ring fixed to the mover and an inner wheel rotatably coupled to an inner periphery of the outer ring, wherein the rotating shaft is coupled to a center of the inner wheel and the shuttle table is joined to an upper surface of the inner wheel.

The shuttle table may be provided with a transfer plate linearly reciprocably mounted to the shuttle table and having a plurality of protrusions on an upper surface thereof. The cradle may be provided with a plurality of insertion holes, into which the protrusions are inserted, corresponding to the protrusions of the transfer plate.

The bridge unit may comprise: a supporting plate horizontally disposed between the rail portion of the waiting room and the rail portion of the MRI room and being movable in a widthwise direction of the rail portions; a connecting plate disposed on the supporting plate and allowing the transfer unit to travel on an upper side thereof; and pivoting means for vertically pivoting the connecting plate with respect to the supporting plate.

The pivoting means may comprise: a first pneumatic or hydraulic cylinder pivotably coupled to a portion of an upper side of the supporting plate at one end thereof and having a movable piston therein; a connecting rod coupled to a leading end of the piston of the cylinder at one end thereof and coupled to the connecting plate at the other end thereof; and a driving portion for actuating the piston of the cylinder.

An upper side of the connecting plate may be provided with at least one rack and a guide rail corresponding to the rack and the guide rail of the rail portions respectively.

The bridge unit may further comprise moving means for horizontally moving the connecting plate to align the rack and the guide rail provided on the connecting plate with the racks and the guide rails provided on the rail portions in a line.

The moving means may comprise: a second pneumatic or hydraulic cylinder fixed to the bridge unit and having a movable piston therein; a first stopper fixed to the supporting plate; a second stopper disposed in the bridge unit to be brought into contact with the first stopper when the rack and the guide rail provided on the connecting plate and the racks and the guide rails provided on the rail portion are aligned with each other; and a spring disposed between a leading end of the piston and the supporting plate. The leading end of the piston may be connected to the supporting plate.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A PET-MRI hybrid system, comprising:

a waiting room having a rail portion at a bottom thereof;

an MRI room containing an MRI apparatus and having a rail portion aligned with the rail portion of the waiting room at a bottom thereof, the MRI room being divided from the waiting room by a shield door;

a PET room containing a PET apparatus, the PET room being positioned to be opposed to the MRI room about the waiting room, wherein the rail portion of the waiting room is extended on a bottom of the PET room;

a transfer unit for supporting a subject lying on an upper side thereof and traveling along the rail portions of the waiting room, the MRI room and the PET room, the transfer unit comprising a mover movable along the rail portions, a shuttle table horizontally sluably mounted to an upper side of the mover, and a cradle slidably mounted on an upper side of the shuttle table; and a bridge unit including a rail portion, the bridge unit selectively shiftable between a first position in which the rail portion of the bridge unit is displaced, providing a space for a movement of the shield door between the rail portion of the waiting room and the rail portion of the MRI room and a second position in which the rail portion of the bridge unit is connected with the rail portion of the waiting room and the rail portion of the MRI room, thereby allowing the transfer unit to be reciprocated between the waiting room and the MRI room.

2. The PET-MRI hybrid system of claim 1, wherein each upper side of the rail portions of the waiting room and the MRI room is provided with at least one rack extending in a lengthwise direction of the rail portions, and
wherein the transfer unit comprises a gear engaged to the rack and a first driving means for generating a driving force for rotating the gear.

3. The PET-MRI hybrid system of claim 2, wherein each upper side of the rail portions of the waiting room and the MRI room is provided with at least one guide rail extending in a lengthwise direction of the rail portions, and wherein the transfer unit further comprises a plurality of moving blocks movable along the guide rail as contacted to the guide rail.

4. The PET-MRI hybrid system of claim 1, wherein the mover comprises a lower section movable as contacted to the rail portions, the mover further comprising an upper section covering an upper side of the lower section and being upward and downward movably mounted to the lower section.

5. The PET-MRI hybrid system of claim 4, wherein the mover comprises: a second driving means for generating a driving force for lifting and lowering the upper section from and to the lower section; a first converting means for converting the driving force of the second driving means into linear motions; and a second converting means for linking the first converting means to the upper section and converting the linear motions of the first converting means into upward and downward motions.

6. The PET-MRI hybrid system of claim 5, wherein the first converting means comprises: a driving pulley rotatable by the second driving means; a driven pulley rotatably disposed on a bottom plate of the lower section; a belt winding around the driving pulley and the driven pulley; a lead screw coupled to a center of the driven pulley at one end thereof to be rotated together therewith and being elongated in an extension direction of the rail portions; and a nut screwed to the lead screw and being linearly moved by a rotation of the lead screw.

7. The PET-MRI hybrid system of claim 6, wherein the second converting means comprises: a connecting shaft coupled to at least one side of the nut and being horizontally extended perpendicular to the lead screw; a first link rotatably coupled to the connecting shaft at a lower end thereof and being rotatably coupled to one side of the upper section at an upper end thereof; and a second link cross-linked to a central portion of the first link and being rotatably coupled to the bottom of the lower section at a lower end thereof and being rotatably coupled to other side of the upper section at an upper end thereof.

8. The PET-MRI hybrid system of claim 7, wherein a bottom plate of the lower section and a top plate of the upper section comprise guide rails extending in a lengthwise direction of the lead screw, and wherein the lower end of the first link and the upper end of the second link comprise moving blocks movable along the guide rails as contacted to the guide rail.

9. The PET-MRI hybrid system of claim 1, wherein the mover comprises: a third driving means for generating a driving force for horizontally slueing the shuttle table; a driving pulley rotatable by the third driving means; a driven pulley connected to the drive pulley by a belt to be rotated together with the driving pulley; a rotating shaft coupled to a center of the driven pulley at one end thereof to be rotated together with the driven pulley; and a wire race bearing including an outer ring fixed to the mover and an inner wheel rotatably coupled to an inner periphery of the outer ring, wherein the rotating shaft is coupled to a center of the inner wheel and the shuttle table is joined to an upper surface of the inner wheel.

10. The PET-MRI hybrid system of claim 1, wherein the shuttle table comprises a transfer plate linearly reciprocably mounted to the shuttle table and having a plurality of protrusions on an upper surface thereof, and wherein a bottom surface of the cradle comprises a plurality of insertion holes, into which the protrusions are inserted, corresponding to the protrusions of the transfer plate.

11. The PET-MRI hybrid system of claim 3, wherein the bridge unit comprises: a supporting plate horizontally disposed between the rail portion of the waiting room and the rail portion of the MRI room and being movable in a widthwise direction of the rail portions; a connecting plate disposed on the supporting plate and allowing the transfer unit to travel on an upper side thereof; and pivoting means for vertically pivoting the connecting plate with respect to the supporting plate.

12. The PET-MRI hybrid system of claim 11, wherein the pivoting means comprises: a first pneumatic or hydraulic cylinder pivotably coupled to a portion of an upper side of the supporting plate at one end thereof and having a movable piston therein; a connecting rod coupled to a leading end of the piston of the cylinder at one end thereof and coupled to the connecting plate at the other end thereof; and a driving portion for actuating the piston of the cylinder.

13. The PET-MRI hybrid system of claim 11 or 12, wherein an upper side of the connecting plate comprises at least one rack and a guide rail corresponding to the rack and the guide rail of the rail portions.

14. The PET-MRI hybrid system of claim 13, wherein the bridge unit comprises moving means for horizontally moving the connecting plate to align the rack and the guide rail provided on the connecting plate with the racks and the guide rails provided on the rail portions in a line.

15. The PET-MRI hybrid system of claim 14, wherein the moving means comprises: a second pneumatic or hydraulic cylinder fixed to the bridge unit and having a movable piston therein; a first stopper fixed to the supporting plate; a second stopper disposed in the bridge unit to be brought into contact with the first stopper when the rack and the guide rail provided on the connecting plate and the racks and the guide rails provided on the rail portion are aligned with each other; and a spring disposed between a leading end of the piston and the supporting plate, and wherein the leading end of the piston is connected to the supporting plate.

* * * * *